(12) United States Patent
Shinozaki et al.

(10) Patent No.: US 6,747,022 B2
(45) Date of Patent: Jun. 8, 2004

(54) CALCIUM SALTS OF 1,5-BENZODIAZEPINE DERIVATIVES, PROCESS FOR PRODUCING THE SALTS AND DRUGS CONTAINING THE SAME

(75) Inventors: Katsuo Shinozaki, Saitama (JP); Masakazu Murata, Saitama (JP); Kiyoto Maeda, Saitama (JP); Hiroaki Taguchi, Saitama (JP); Nobuo Kawase, Saitama (JP); Naoyoshi Miura, Saitama (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 19 days.

(21) Appl. No.: 10/130,305

(22) PCT Filed: Dec. 1, 2000

(86) PCT No.: PCT/JP00/08511
§ 371 (c)(1),
(2), (4) Date: Aug. 15, 2002

(87) PCT Pub. No.: WO01/40197
PCT Pub. Date: Jun. 7, 2001

(65) Prior Publication Data
US 2003/0096809 A1 May 22, 2003

(30) Foreign Application Priority Data
Dec. 2, 1999 (JP) .............................. 11-342799

(51) Int. Cl.[7] .................. C07D 243/12; A61K 31/551; A61P 1/04
(52) U.S. Cl. .................................... 514/221; 540/517
(58) Field of Search ........................... 540/517; 514/221

(56) References Cited

U.S. PATENT DOCUMENTS

6,239,131 B1    5/2001   Shinozaki et al. ............ 514/221
6,344,452 B1    2/2002   Shinozaki et al. ............ 514/221

FOREIGN PATENT DOCUMENTS

EP    945445      9/1999
JP    61-63666    4/1986
JP    63-238069   10/1988
WO    94/00438    1/1994
WO    95/18110    7/1995
WO    99/64403    12/1999

OTHER PUBLICATIONS

J.R. Grider et al.: "Distinct receptors for cholecystokinin and gastrin on muscle cells of stomach and gallbladder" The American Physiological Society, pp. G184–G190 1990.
Folia Pharmacologica Japonica, vol. 106, pp. 171–180 1995.
Francesco Makovec: "CCK–B/gastrin–receptor antagoinsts" Drugs of the Future, vol. 18, pp. 919–931 1993.
Stephen A. Wank: "Cholecystokinin receptors" American Journal of Physiology, vol. 269, pp. G628–G646 1995.
Fernando Hernando et al.: "The $CCK_B$ receptor antagonist, L–365,260, elicits antidepressant–type effects in the forced–swim test in mice" European Journal of Pharmacology, vol. 261, pp. 257–263.
Louise Stanfa et al.: "Cholecystokinin and morphine analgesia: variations on a theme" Trends in Pharmacological Science, vol. 15, pp. 65–66 03/94.

*Primary Examiner*—Bruck Kifle
(74) *Attorney, Agent, or Firm*—Oblon, Spivak, McClelland, Maier & Neustadt, P.C.

(57) ABSTRACT

Provided are calcium salts of a 1,5-benzodiazepine derivative represented by the following formula (I):

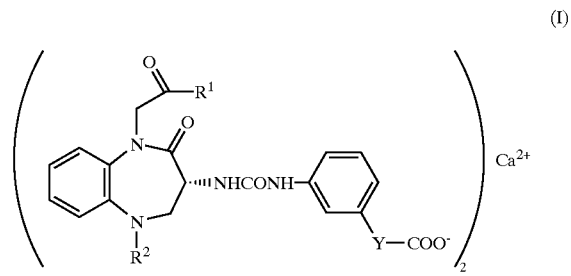

(wherein, $R^1$ represents a lower alkyl group, $R^2$ represents a phenyl or cyclohexyl group, and Y represents a single bond or a lower alkylene group); a process for preparing the salts; and drugs containing the same as the active ingredient.

The compounds exhibit a potent inhibitory activity against the secretion of gastric acid and potent antagonism against gastrin and/or CCK-B receptor.

25 Claims, No Drawings

CALCIUM SALTS OF 1,5-BENZODIAZEPINE DERIVATIVES, PROCESS FOR PRODUCING THE SALTS AND DRUGS CONTAINING THE SAME

TECHNICAL FIELD

The present invention relates to benzodiazepine derivatives having an important role in a medical field. More specifically, the invention relates to calcium salts of 1,5-benzodiazepine derivatives having a gastrin and/or CCK-B (cholecystokinin-B) receptor antagonism and at the same time having potent gastric acid secretion inhibitory action; preparation processes of the compounds; and drugs containing the compounds as an effective ingredient.

BACKGROUND ART

Cholecystokinin (CCK) is a gastrointestinal hormone which is produced by and released from duodenal and jejunal mucous membranes, and is known to have actions such as secretion of pancreatic juice, gallbladder constriction, and stimulation of insulin secretion. CCK is also known to be present in the cerebral cortex, hypothalamus, and hippocampus at a high concentration and exhibit actions such as inhibition of eating and hunger, augmentation of memory, and generation of anxiety. Gastrin is a gastrointestinal hormone which is produced by and released from G-cells distributed in the pylorus and is known to exhibit actions such as secretion of gastric acid and constriction of the pylorus and gallbladder. CCK and gastrin, having the same five amino acids in their C-terminals, express actions via receptors. CCK receptors are classified into CCK-A which are peripheral type receptors distributed in the pancreas, gallbladder, and intestines; and CCK-B which are central type receptors distributed in the brain. Since gastrin receptors and CCK-B receptors show similar properties in receptor-binding tests and have high homology, they are often called CCK-B/gastrin receptors. Compounds having antagonism to these receptors, for example, gastrin or CCK-B receptor, are presumed to be useful for prevention or treatment of gastric ulcer, duodenal ulcer, gastritis, reflux esophagitis, pancreatitis, Zollinger-Ellison syndrome, vacuolating G-cell hyperplasia, basal-mucous-membrane hyperplasia, cholecystitis, attack of biliary colic, dysmotilities of alimentary canal, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms. Moreover, the compounds are expected to induce pain relief or to accelerate induction of pain relief by opioid medications (Folia Pharmacologica Japonica, Vol. 106, 171–180 (1995), Drugs of the Future, Vol. 18. 919–931 (1993), American Journal of Physiology, Vol. 269, G628–G646 (1995), American Journal of Physiology, Vol. 259, G184–G190 (1990), European Journal of Pharmacology, 261, 257–263 (1994), Trends in Pharmacological Science, Vol. 15, 65–66 (1994)).

As a gastrin receptor antagonist, proglumide is known as a remedy for gastric ulcer and gastritis. Proglumide's affinity with gastrin or CCK-B receptors is however very low, and its curative effect is weak. It is reported that some benzodiazepine derivatives such as L-364,718 (devazepide, Japanese Patent Application Laid-Open (kokai) No. 63666/1986) and L-365,260 (Japanese Patent Application Laid-Open (kokai) No. 238069/1988) exhibit CCK-A receptor antagonism or CCK-B receptor antagonism. It is also disclosed that compounds having strong CCK-B receptor antagonism suppress pentagastrin-stimulated secretion of gastric acid (WO 94/438 and WO 95/18110). Administration in vivo of these compounds however does not always bring about satisfactory effects. In WO98/25911 and WO99/64403, the present inventors therefore disclosed 1,5-benzodiazepine derivatives having potent gastrin and/or CCK-B receptor antagonism and at the same time, having strong gastric acid secretion inhibitory action. There is however a demand for compounds which have potent gastrin and/or CCK-B receptor antagonism and gastric acid secretion inhibitory action, particularly strong in gastric acid secretion inhibitory action, and are suited for clinical use.

DISCLOSURE OF THE INVENTION

With the foregoing in view, the present inventors have carried out an extensive investigation. As a result, it has been found that compared with 1,5-benzodiazepine derivatives as specifically described in WO98/25911 and WO99/64403, calcium salts of 1,5-benzodiazepine derivatives having a specific structure, which salts fall within a range disclosed in WO98/25911 and WO99/64403 but are not specifically described therein, have markedly potent inhibitory activity against gastric acid secretion; and owing to low hygroscopicity and easy purification, are desirable as drugs from the viewpoint of quality maintenance so that they are useful as drugs, particularly preventives or remedies for various diseases of digestive tracts resulting from excessive secretion of gastric acid, leading to the completion of the invention.

In one aspect of the present invention, there are thus provided a calcium salt of a 1,5-benzodiazepine derivative represented by the following formula (I):

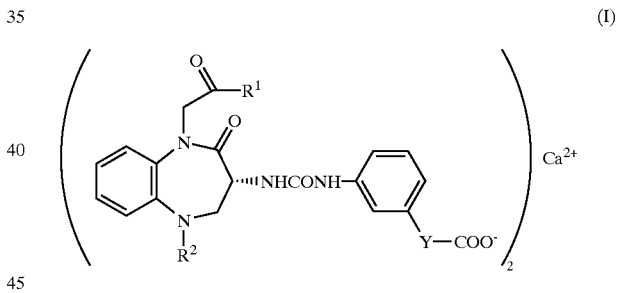

(wherein, $R^1$ represents a lower alkyl group, $R^2$ represents a phenyl or cyclohexyl group, and Y represents a single bond or a lower alkylene group); and a preparation process of the calcium salt.

In another aspect of the invention, there is also provided a gastric acid secretion inhibitor, which comprises, as an effective ingredient, a calcium salt of a 1,5-benzodiazepine derivative represented by the formula (I).

In a further aspect of the invention, there is also provided a drug comprising, as an effective ingredient, a calcium salt of a 1,5-benzodiazepine derivative represented by the formula (I), particularly, a preventive or remedy for gastric ulcer, duodenal ulcer, gastritis, reflux esophagitis or Zollinger-Ellison syndrome.

In a still further aspect of the invention, there is also provided a pharmaceutical composition comprising a calcium salt of a 1,5-benzodiazepine derivative represented by the formula (I) and a pharmaceutically acceptable carrier, particularly, a pharmaceutical composition for preventing and/or treating gastric ulcer, duodenal ulcer, gastritis, reflux esophagitis or Zollinger-Ellison syndrome.

In a still further aspect of the present invention, there is also provided the use of a calcium salt of a 1,5-benzodiazepine derivative represented by the formula (I) for the preparation of a preventive and/or remedy for gastric ulcer, duodenal ulcer, gastritis, reflux esophagitis or Zollinger-Ellison syndrome.

In a still further aspect of the present invention, there is also provided a treating method of gastric ulcer, duodenal ulcer, gastritis, reflux esophagitis or Zollinger-Ellison syndrome, which comprises administering a calcium salt of a 1,5-benzodiazepine derivative represented by the formula (I).

BEST MODE FOR CARRYING OUT THE INVENTION

The term "lower" as used herein means a linear or branched carbon chain having 1 to 4 carbon atoms.

Accordingly, examples of the "lower alkyl group" include methyl, ethyl, propyl, isopropyl, butyl, isobutyl, sec-butyl and tert-butyl, while those of the "lower alkylene group" include methylene, ethylene, propylene, butylene, methylmethylene, dimethylmethylene, 1-methylethylene, 1,1-dimethylethylene, 1-methylpropylene and 2-methylpropylene.

The term "halogen atom" as used herein means a fluorine, chlorine, bromine or iodine atom.

The term "metal atom" as used herein means a metal atom which can be converted into a monovalent or divalent cation and examples include sodium, potassium and calcium atoms.

It is preferred that in the formula (I), $R^1$ represents a branched $C_4$ alkyl group, particularly, a tert-butyl group; $R^2$ represents a cyclohexyl group and Y represents a single bond or dimethylmethylene.

The present invention not only embraces optically active isomers and diastereomers but also solvates such as hydrates and polymorphs.

Of the invention compounds (I), particularly preferred from the viewpoint of inhibitory action against gastric acid secretion and storage stability are calcium (R)-(−)-3-[3-(1-tert-butylcarbonylmethyl-2-oxo-5-cyclohexyl-1,3,4,5-tetrahydro-2H-1,5-benzodiazepin-3-yl)ureido]benzoate (Compound of Example 1) and calcium (R)-(−)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionate (Compound of Example 4), with Compound of Example 1 being still more preferred.

The invention compounds (I) can be prepared by various synthesis processes in consideration of their essential skeleton or features of the constituent groups. The following are typical preparation processes of them. Preparation Process A:

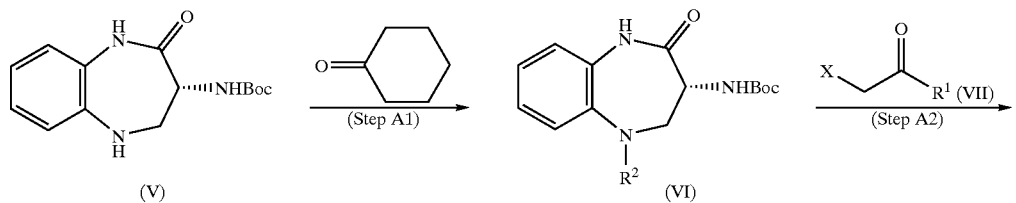

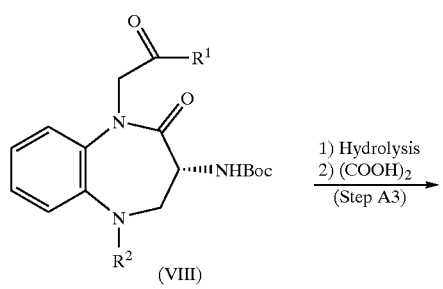

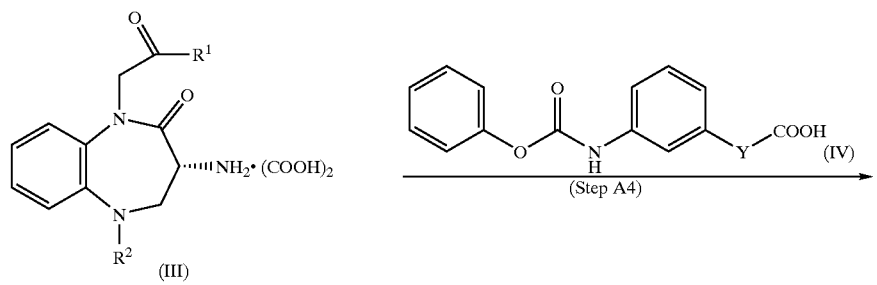

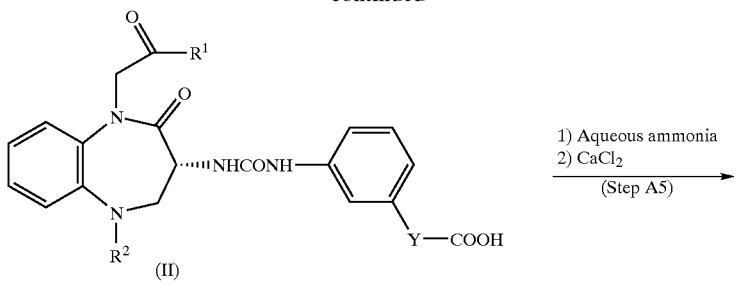

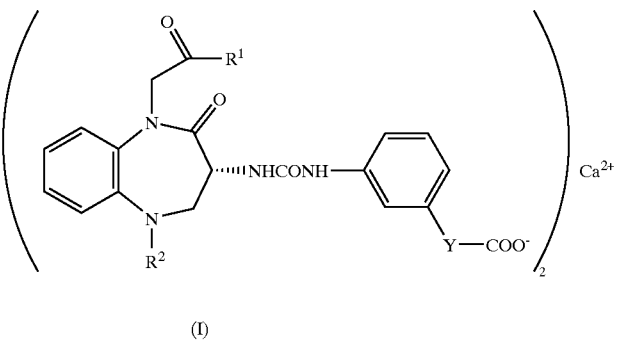

(wherein, $R^1$, $R^2$ and Y have the same meanings as described above, Boc represents a tert-butoxycarbonyl group and X represents a halogen atom).

Step A1

Reaction of a 3-substituted aminobenzodiazepine derivative (V) with cyclohexanone leads to preparation of the corresponding 5-substituted derivative (VI). For the preparation of the 5-substituted derivative (VI) having a cyclohexyl group as $R^2$, a catalyst such as platinum oxide or palladium carbon is added to a solution of the derivative (V) dissolved in acetic acid, followed by stirring under normal pressure or under pressure in a hydrogen atmosphere. Usually, this reaction can be carried out at room temperature, under warming or under heating. For the preparation of a 5-substituted derivative (VI) having a phenyl group as $R^2$, on the other hand, a hydrogen acceptor such as cyclooctene or nitrobenzene is added to the derivative (V) in a solventless manner or in a solvent inert to the reaction such as xylene, and then a catalyst such as palladium carbon is added, followed by stirring. Usually, this reaction can be carried out under warming or heating.

Step A2

Reaction of the 5-substituted derivative (VI) with a halomethyl ketone compound (VII) leads to preparation of the corresponding 1,5-substituted derivative (VIII). This reaction is usually conducted by adding a base such as sodium hydride, potassium carbonate or potassium tert-butoxide to the 5-substituted derivative (VI), adding the compound (VII) to the resulting mixture and then adding, if necessary, a phase transfer catalyst such as tetrabutylammonium bromide. For the reaction, any solvent inert to the reaction is usable. Usually employed is an ether solvent such as tetrahydrofuran or dioxane, toluene, ethyl acetate, N,N-dimethylformamide or dimethylsulfoxide. Alternatively, the reaction can be effected in a two phase system such as water-toluene in the presence of a phase transfer catalyst such as tetrabutylammonium bromide. The reaction is usually conducted within a temperature range of −78 to 150° C.

Step A3

The 1,5-substituted derivative (VIII) can be converted into an oxalate (III) of a 3-amino-1,5-benzodiazepine derivative after deprotection. The deprotection is effected by adding an acid such as hydrochloric acid or trifluoroacetic acid to the derivative (VIII). This reaction is usually conducted in the presence or absence of a solvent within a temperature range of from 0 to 100° C. Examples of the solvent usable here include alcohols such as methanol and ethanol, halogen solvents such as chloroform and ether solvents such as dioxane and diethyl ether. The subsequent conversion into an oxalate is conducted in a manner known per se in the art by adding oxalic acid or hydrate thereof to the hydrolyzate obtained by the above-described reaction.

Step A4

Reaction of the oxalate (III) of a 3-amino-1,5-benzodiazepine derivative with Compound (IV) leads to preparation of the corresponding 1,5-benzodiazepine derivative (II). This reaction is usually conducted in the presence or absence of a base such as triethylamine within a range of 0° C. to reflux temperature. For the reaction, any solvent inert to the reaction can be used and N,N-dimethylformamide or dimethylsulfoxide is usually employed.

Step A5

Aqueous ammonia is then added to the 1,5-benzodiazepine derivative (II), followed by treatment of the mixture by adding thereto a calcium chloride solution, whereby the invention compound (I) can be prepared. This reaction is usually conducted by adding aqueous ammonia under ice cooling, at room temperature, under warming or under heating; stirring the mixture; and then adding a calcium chloride solution. For this reaction, any solvent one inert to the reaction can be used and ethanol is usually employed.

Preparation Process B

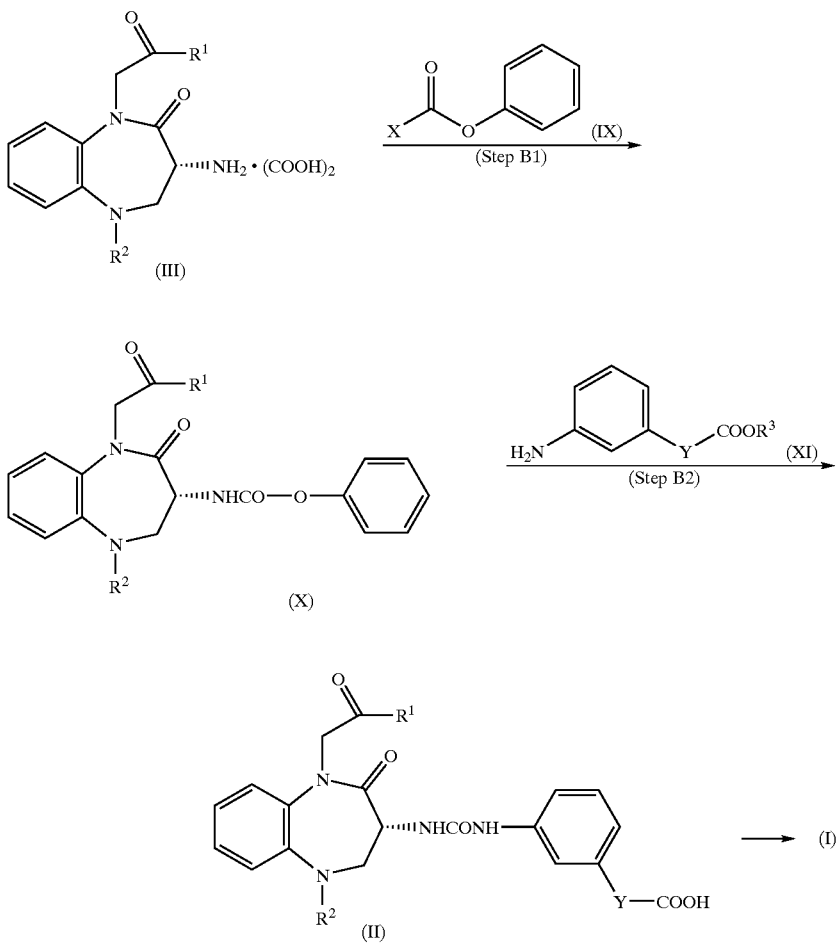

(wherein, $R^1$, $R^2$ and Y have the same meanings as described above, $R^3$ represents a hydrogen atom or a metal atom and X represents a halogen atom).

Step B1

Reaction of the oxalate (III) of a 3-amino-1,5-benzodiazepine derivative with Compound (IX) leads to preparation of the corresponding 3-phenoxycarbonylamino derivative (X). This reaction is usually conducted under ice cooling, at room temperature, under warming or under heating in the presence or absence of a base such as potassium carbonate or triethylamine. For the reaction, any solvent inert to the reaction is usable and ethyl acetate, tetrahydrofuran or N,N-dimethylformamide is usually employed.

Step B2

By adding an aniline derivative (XI) to the 3-phenoxycarbonylamino phenoxycarbonylamino derivative (X), the corresponding 1,5-benzodiazepine derivative (II) can be prepared. This reaction is usually carried out in the presence or absence of a base such as triethylamine or potassium carbonate within a range of 0° C. to reflux temperature. For the reaction, any solvent inert to the reaction is usable and usually employed is dimethylsulfoxide or N,N-dimethylformamide.

The 1,5-benzodiazepine derivative (II) obtained in Step B2 can be introduced into the invention compound (I) in accordance with step A5 of Preparation Process A.

The invention compound (I) thus prepared is isolated and then purified by the ordinarily employed operation selected as needed from extraction, concentration, evaporation, crystallization, filtration, recrystallization, pulverization, and chromatography. The optically active invention compound (I) can be produced using a proper raw material compound, or by ordinarily employed racemic resolution method such as a method of introducing the compound into the corresponding diastereomer salt with a typical optically active acid such as dibenzoyl tartrate, followed by optical resolution; or a method of introducing the compound into the corresponding diastereomer compound, separating it and then subjecting the separated compound to Edman degradation.

The invention compound (I) can be administered orally or parenterally after incorporation therein a pharmaceutically acceptable carrier or adjuvant. For oral administration, the compound of the present invention may be formed into solid preparations such as tablets, powder, and capsules by using, in combination, proper additives, for example, excipients such as lactose, mannitol, corn starch, and crystalline cellulose; binders such as cellulose derivatives, gum arabic, and gelatin; disintegrators such as carboxymethyl cellulose calcium; lubricants such as talc and magnesium stearate. These solid preparations may be formed into enteric coating preparations by using a coating base such as hydroxypropyl methylcellulose phthalate, hydroxypropyl methylcellulose acetate succinate, cellulose acetate phthalate or methacrylate copolymer. Alternatively, they may be formed into liquid preparations such as solutions, suspensions, and emulsions.

For parenteral administration, the compound of the present invention may be formed into a liquid formulation for injection by using, in combination, water, ethanol, glycerin or ordinarily employed surfactant. It may also be formed into a suppository by using a suppository base.

The dose of the invention compound (I) varies depending on the dosage form, administration route, age, or symptoms. Orally, the dose is 1–1,000 mg, preferably 5–500 mg, per day for an adult and it is preferably administered once or 2 to 3 portions a day.

As described later, invention compounds (I) exhibit strong inhibitory action against secretion of gastric acid compared with the compounds as described in WO98/25911 and WO99/64403. In addition, they have low hygroscopicity and can be purified readily so that from the viewpoint of maintenance of its quality, they are excellent as a drug. Moreover, they exhibit potent antagonism against gastrin and/or CCK-B receptor, and therefore, they are useful for treatment, amelioration, or prevention of various diseases of digestive tracts resulting from excessive secretion of gastric acid, for example, gastric ulcer, duodenal ulcer, gastritis, reflux esophagitis, pancreatitis and Zollinger-Ellison syndrome. They are also useful for the treatment, amelioration or prevention of diseases related to gastrin and/or CCK-B receptor antagonism, such as vacuolating G-cell hyperplasia, basal-mucous-membrane hyperplasia, cholecystitis, attack of biliary colic, dysmotilities of alimentary canal, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms; and induction of pain relief or augmentation of induction of pain relief by an opioid medication.

EXAMPLES

The present invention will hereinafter be described by Examples. It should however be borne in mind that the invention is not limited to or by them.

EXAMPLE 1

Preparation of calcium (R)-(−)-3-[3-(1-tert-butylcarbonylmethyl-2-oxo-5-cyclohexyl-1,3,4,5-tetrahydro-2H-1,5-benzodiazepin-3-yl)ureido]benzoate

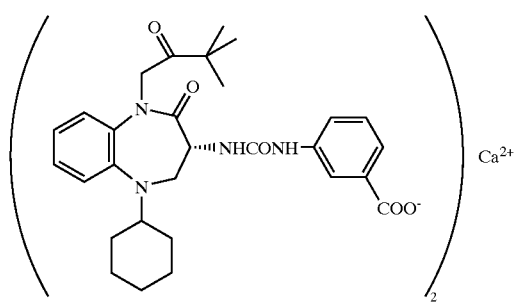

Step 1

Preparation of (R)-(−)-2-oxo-3-tert-butoxycarbonylamino-5-cyclohexyl-1,3,4,5-tetrahydro-2H-1,5-benzodiazepine.

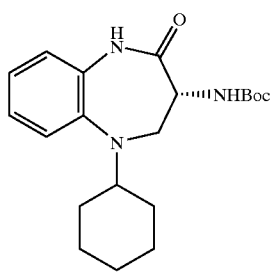

To a solution of 50 g of (R)-(+)-2-oxo-3-tert-butoxycarbonylamino-1,3,4,5-tetrahydro-2H-1,5-benzodiazepine as described in WO98/25911 in 43.3 g of acetic acid were added 70.8 g of cyclohexanone and 1.5 g of platinum oxide. The resulting mixture was stirred at room temperature for 5 hours under pressure of 3 to 3.5 kg/cm$^2$ in a hydrogen gas atmosphere. To the reaction mixture were added 200 ml of ethyl acetate and 5 g of active charcoal, followed by stirring for further 1 hour at room temperature. The reaction mixture was filtered. A 2N aqueous solution of sodium hydroxide was added dropwise to the filtrate to neutralize the same under stirring and then, it was separated into layers. The organic layer was successively washed with a saturated aqueous solution of sodium bicarbonate and brine, and dried over anhydrous sodium sulfate. The solvent was evaporated under reduced pressure. To the residue were added 200 ml of ethanol and 200 ml of water. The mixture was stirred at 50° C. for 1 hour and then for 2 hours under ice cooling. Crystals so precipitated were collected by filtration with suction, washed with a mixed solvent of ethanol and water (1:1) and then dried to obtain 59.3 g of the title compound.

Melting point: 156 to 159° C.

$^1$H-NMR (CDCl$_3$)δ: 1.11–2.07(19H,m), 3.15–3.27(1H, m), 3.33(1H,dd), 3.68(1H,dd), 4.38–4.49(1H,m), 5.53(1H, d), 6.91–6.96(2H,m), 7.11–7.16(2H,m), 7.45(1H,brs).

[α]D$^{23}$: −188'(C=1.02, CHCl$_3$)

Incidentally, 2-oxo-3-tert-butoxycarbonylamino-5-cyclohexyl-1,3,4,5-tetrahydro-2H-1,5-benzodiazepine was also prepared by the below-described operation.

In 1.2 g of acetic acid were dissolved 1.39 g of 2-oxo-3-tert-butoxycarbonylamino-1,3,4,5-tetrahydro-2H-1,5-benzodiazepine and 3.9 g of cyclohexanone. To the resulting solution was added 302 mg of 10% palladium carbon. Under a hydrogen pressure of 10 kg/cm$^2$, the mixture was stirred at 50 to 55° C. for 12 hours. After the reaction mixture was cooled to room temperature, the reaction mixture was filtered through Celite. Water was added to the filtrate and crystals so precipitated were collected by filtration with suction. The resulting crystals were recrystallized from a mixed solvent of ethanol and water, whereby 1.63 g of the title compound was obtained.

Step 2

Preparation of (R)-1-tert-butylcarbonylmethyl-2-oxo-3-tert-butoxycarbonylamino-5-cyclohexyl-1,3,4,5-tetrahydro-2H-1,5-benzodiazepine

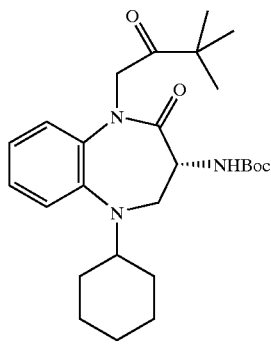

To a solution of 50 g of (R)-(−)-2-oxo-3-tert-butoxycarbonylamino-5-cyclohexyl-1,3,4,5-tetrahydro-2H-1,5-benzodiazepine in 200 ml of dimethylsulfoxide were added 28.1 g of 1-chloropinacolone, 28.8 g of potassium carbonate (powder), 1.15 g of potassium iodide and 1.35 g of tetrabutylammonium bromide. The mixture was stirred at room temperature for 4 hours. The reaction mixture was poured into ice water. The precipitate thus formed was collected by filtration with suction, washed with water and then dried, whereby 63.5 g of the title compound was obtained.

$^1$H-NMR (CDCl$_3$)δ: 1.15–2.07(28H,m), 3.13–3.24(1H,m), 3.26(1H,dd), 3.61(1H,dd), 4.11(1H,d), 4.39–4.50(1H,m), 5.17(1H,d), 5.57(1H,d), 6.92–7.03(2H,m), 7.12–7.20(2H,m).

Step 3

Preparation of (R)-(−)-1-tert-butylcarbonylmethyl-2-oxo-3-amino-5-cyclohexyl-1,3,4,5-tetrahydro-2H-1,5-benzodiazepine oxalate monohydrate and (R)-(−)-1-tert-butylcarbonylmethyl-2-oxo-3-amino-5-cyclohexyl-1,3,4,5-tetrahydro-2H-1,5-benzodiazepine oxalate

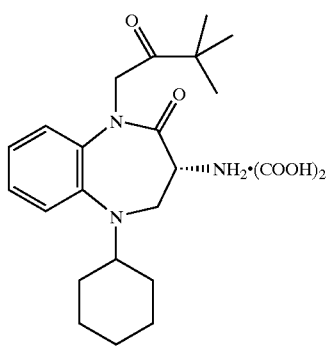

To a solution of 63.5 g of (R)-1-tert-butylcarbonylmethyl-2-oxo-3-tert-butoxycarbonylamino-5-cyclohexyl-1,3,4,5-tetrahydro-2H-1,5-benzodiazepine in 100 ml of ethanol were added 100 ml of 6N hydrochloric acid. The mixture was stirred at 60° C. for 1.5 hours. After the reaction mixture was cooled to room temperature, a mixed solvent of water and diethyl ether (1:1) was added. The aqueous layer was separated, neutralized with a 6N aqueous solution of sodium hydroxide, and then extracted with ethyl acetate. The extract was washed with brine, dried over anhydrous sodium sulfate and evaporated under reduced pressure, whereby 46.3 g of (R)-(−)-1-tert-butylcarbonylmethyl-2-oxo-3-amino-5-cyclohexyl-1,3,4,5-tetrahydro-2H-1,5-benzodiazepine was obtained.

$^1$H-NMR (CDCl$_3$)δ: 1.11–2.08(2H,m), 3.12–3.27(2H,m), 3.40(1H,dd), 3.53–3.62(1H,m), 4.01(1H,d), 5.29(1H,d), 6.92–7.04(2H,m), 7.15–7.19(2H,m)

[α]D$^{25}$: −28.9° (C=1.04, MeOH)

The (R)-(−)-1-tert-butylcarbonylmethyl-2-oxo-3-amino-5-cyclohexyl-1,3,4,5-tetrahydro-2H-1,5-benzodiazepine thus obtained was dissolved in 550 ml of ethyl acetate. To the resulting solution was added 16.31 g of oxalic acid dihydrate to dissolve the latter in the former. Then, 367 ml of n-hexane was added and the mixture was stirred overnight. Crystals so precipitated were collected by filtration with suction, washed with a mixed solvent of ethyl acetate and n-hexane (1:1), and then dried, whereby 55 g of (R)-(−)-1-tert-butylcarbonylmethyl-2-oxo-3-amino-5-cyclohexyl-1,3,4,5-tetrahydro-2H-1,5-benzodiazepine oxalate monohydrate was obtained.

Melting point: 97 to 99° C.

$^1$H-NMR (DMSO-d$_6$)δ: 1.10–1.83(18H,m), 1.93–2.07 (1H,m), 3.15–3.28(1H,m), 3.39–3.57(2H,m), 3.88(1H,dd), 4.47(1H,d), 5.10(1H,d), 6.70(6H,br), 7.03–7.16(2H,m), 7.22–7.33(2H,m).

[α]D$^{27}$: −12.2° (C=1.00, MeOH)

Elemental analysis: (C) 59.15, (H) 7.45, (N) 9.03 (C$_{21}$H$_{31}$N$_3$O$_2$·C$_2$H$_2$O$_4$·H$_2$O)

In 10 ml of ethyl acetate was dissolved 1 g of (R)-(−)-1-tert-butylcarbonylmethyl-2-oxo-3-amino-5-cyclohexyl-1,3,4,5-tetrahydro-2H-1, 5-benzodiazepine. Oxalate anhydride (252 mg) was added to the resulting solution, followed by stirring overnight. Crystals so precipitated were collected by filtration with suction, washed with ethyl acetate and then dried to obtain 1.05 g of (R)-(−)-1-tert-butylcarbonylmethyl-2-oxo-3-amino-5-cyclohexyl-1,3,4,5-tetrahydro-2H-1,5-benzodiazepine oxalate.

Melting point: 147 to 150° C.

$^1$H-NMR (DMSO-d$_6$)δ: 1.10–1.83(18H,m), 1.93–2.07 (1H,m), 3.15–3.28(1H,m), 3.39–3.57(2H,m), 3.88(1H,dd), 4.47(1H,d), 4.70(4H,br), 5.10(1H,dd), 7.03–7.16(2H,m), 7.22–7.33(1H,m).

[α]D$^{27}$: −13.3° (C=1.00, MeOH)

Elemental analysis: (C) 61.67, (H) 7.47, (N) 9.28 (C$_{21}$H$_{31}$N$_3$O$_2$·C$_2$H$_2$O$_4$)

Step 4

Preparation of 3-phenyloxycarbonylaminobenzoic acid

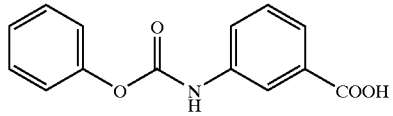

After 274.3 g of 3-aminobenzoic acid was dissolved in 4L of a 0.5N aqueous solution of sodium hydroxide, a solution of 328.8 g of phenyl chloroformate in 1L of tetrahydrofuran was added dropwise at 10° C. The reaction mixture was stirred at the same temperature for 1 hour, and then at room temperature for 1 hour. Crystals so precipitated were collected by filtration with suction, washed with water, dried and then recrystallized from ethanol to obtain 412 g of the title compound.

Melting point: 131 to 133° C.

$^1$H-NMR (DMSO-d$_6$)δ: 7.21–7.32(3H,m), 7.40–7.49(3H,m), 7.61–7.66(1H,m), 7.71–7.77(1H,m), 8.16(1H,t), 10.42 (1H,s), 12.96(1H,brs)

Step 5
Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]benzoic acid monohydrate

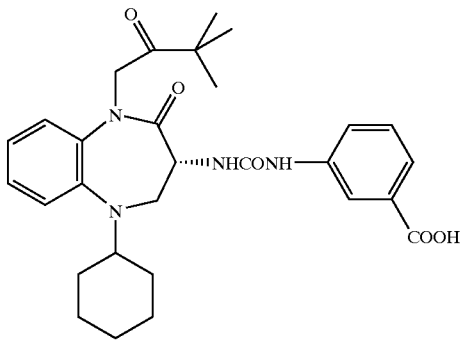

To a solution of 51.2 g of (R)-(−)-1-tert-butylcarbonylmethyl-2-oxo-3-amino-5-cyclohexyl-1,3,4,5-tetrahydro-2H-1,5-benzodiazepine oxalate monohydrate in 550 ml of anhydrous dimethylsulfoxide were added 28.0 g of 3-(N-phenoxycarbonyl)aminobenzoic acid and 44.5 g of triethylamine. The resulting mixture was stirred at 60 to 65° C. for 2 hours. Ethanol (550 ml) was then added to the reaction mixture. Under ice cooling, 550 ml of 1N hydrochloric acid was added dropwise and the mixture was stirred at room temperature for 2 hours. Crystals so precipitated were collected and recrystallized from a mixed solvent of ethanol and water, whereby 46.3 g of the title compound was obtained as colorless crystals.

Melting point: 159 to 161° C.
$^1$H-NMR (DMSO-d$_6$)δ: 1.05–2.08(19H,m), 3.16–3.49 (3H,m), 4.33–4.40(1H,m), 4.39(1H,d), 5.12(1H,d), 6.62(1H, d), 6.98–7.14(2H,m), 7.23–7.36(3H,m), 7.44–7.52(2H,m), 7.99(1H,brs), 9.06(1H,brs), 11.50(1H,br)
MS(FAB)m/z: 521 (MH$^+$), 543(M+Na)$^+$
IR(KBr)cm$^{-1}$: 3370, 2932, 2855, 1727, 1644, 1561, 1497
[α]D$^{25}$: −148° (C=1.0, CHCl$_3$)
Elemental analysis: (C) 64.32, (H) 7.41, (N) 10.16 (C$_{29}$H$_{36}$N$_4$O$_5$.0.5C$_2$H$_5$OH.H$_2$O)

Step 6
Preparation of calcium (R)-(−)-3-[3-(1-tert-butylcarbonylmethyl-2-oxo-5-cyclohexyl-1,3,4,5-tetrahydro-2H-1,5-benzodiazepin-3-yl)ureido]benzoate

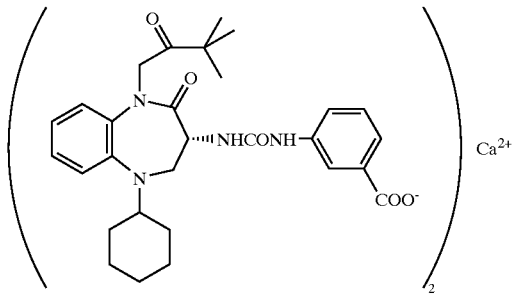

In 220 ml of ethanol was suspended 22.0 g of (R)-(−)-3-[3-(1-tert-butylcarbonylmethyl-2-oxo-5-cyclohexyl-1,3,4,5-tetrahydro-2H-1,5-benzodiazepin-3-yl)ureido]benzoic acid monohydrate. Under ice cooling, the resulting suspension was dissolved in 26.4 ml of concentrated aqueous ammonia. To the reaction mixture was added 22 ml of an aqueous solution of 3.05 g of calcium chloride, followed by stirring for 30 minutes. Water was added. The precipitate was collected by filtration and washed with a mixed solvent of water and ethanol (2:1), whereby 21.0 g of the title compound as powder was obtained.

$^1$H -NMR (DMSO-d$_6$)δ: 0.94–1.96(38H,m), 3.21–3.44 (6H,m), 4.36–4.43(4H,m), 5.12(2H,d), 6.77(2H,d), 7.00–7.29(10H,m), 7.52–7.56(4H,m), 7.90(2H,s), 9.16(2H, s).
MS(FAB)m/z: 1079(MH$^+$), 559, 521
IR(KBr)cm$^{-1}$: 2932, 2361, 1662, 1552, 1498, 1396, 1217, 767
[α]D$^{26}$: −66.1° (C=1, MeOH)

EXAMPLE 2
Preparation of (R)-(−)-3-[3-(1-tert-butylcarbonylmethyl-2-oxo-5-cyclohexyl-1,3,4,5-tetrahydro-2H-1,5-benzodiazepin-3-yl)ureido]benzoic acid

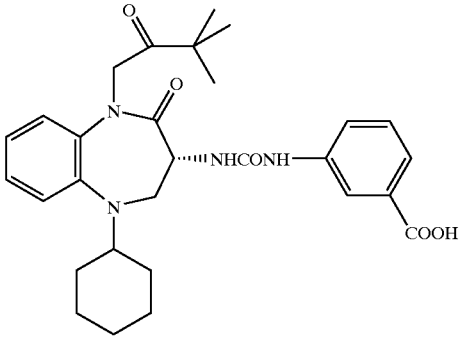

Step 1
Preparation of (R)-(−)-1-tert-butylcarbonylmethyl-2-oxo-3-phenoxycarbonylamino-5-cyclohexyl-1,3,4,5-tetrahydro-2H-1,5-benzodiazepine

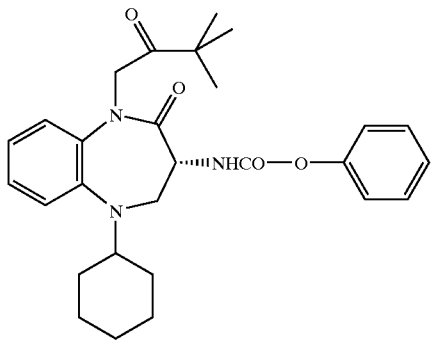

To a suspension of 8.9 g of (R)-(−)-1-tert-butylcarbonylmethyl-2-oxo-3-amino-5-cyclohexyl-1,3,4,5-tetrahydro-2H-1,5-benzodiazepine oxalate in 45 ml of ethyl acetate was added 45 ml of an aqueous solution of 8.25 g of potassium carbonate under ice cooling. The mixture was stirred at the same temperature for 30 minutes. After addition of 3.12 g of phenyl chlorocarbonate under ice cooling, the mixture was stirred for 5 minutes under ice cooling and then at room temperature for 30 minutes. The reaction mixture was then separated into layers. The aqueous layer was extracted with ethyl acetate and the organic layer thus obtained was combined with the organic layer obtained in advance. The combined organic layer was washed with brine, dried over anhydrous sodium sulfate and evaporated under reduced pressure, whereby 9.19 g of the title compound was obtained.

$^1$H-NMR (CDCl$_3$)δ: 1.10–1.90(9H,m), 1.28(9H,s), 1.97–2.08(1H,m), 3.14–3.27(1H,m), 3.38(1H,dd), 3.73(1H, dd), 4.15(1H,d), 4.53(1H,dt), 5.20(1H,d), 6.11(1H,d), 6.93–7.24(7H,m), 7.28–7.36(2H,m).

[α]D: –45.6 (C=1.0, CHCl₃)

Step 2
Preparation of (R)-(–)-3-[3-(1-tert-butylcarbonylmethyl-2-oxo-5-cyclohexyl-1,3,4,5-tetrahydro-2H-1,5-benzodiazepin-3-yl)ureido]benzoic acid

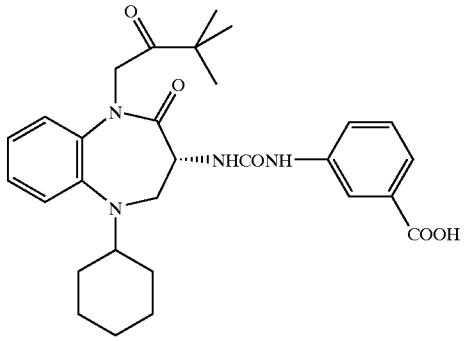

Under an argon atmosphere, 2.0 g of sodium 3-aminobenzoate, 77 mg of 4-dimethylaminopyridine and 3.0 g of Molecular Sieves 3A were added to a solution of 3.0 g of (R)-(–)-1-tert-butylcarbonylmethyl-2-oxo-3-phenoxycarbonylamino-5-cyclohexyl-1,3,4,5-tetrahydro-2H-1,5-benzodiazepine in 30 ml of anhydrous dimethylsulfoxide. The mixture was stirred at room temperature for 15 hours. After filtration of the reaction mixture, ice water and a 1N aqueous solution of sodium hydroxide were added to the filtrate. The mixture was extracted with ethyl acetate. The organic layer was washed successively with a 1N aqueous solution of sodium hydroxide, 1N hydrochloric acid and brine, dried over anhydrous sodium sulfate and evaporated under reduced pressure. To the residue was added a mixed solvent of ethanol and water (2:1). Crystals so precipitated were collected by filtration, whereby 2.32 g of the title compound was obtained.

The (R)-(–)-3-[3-(1-tert-butylcarbonylmethyl-2-oxo-5-cyclohexyl-1,3,4,5-tetrahydro-2H-1,5-benzodiazepin-3-yl)ureido]benzoic acid obtained in Step 2 was treated in a similar manner to Step 6 of Example 1, whereby calcium (R)-(–)-3-[3-(1-tert-butylcarbonylmethyl-2-oxo-5-cyclohexyl-1,3,4,5-tetrahydro-2H-1,5-benzodiazepin-3-yl)uteido]benzoate was prepared.

EXAMPLE 3

Preparation of calcium (R)-(–)-3-[3-(1-tert-butylcarbonylmethyl-2-oxo-5-phenyl-1,3,4,5-tetrahydro-2H-1,5-benzodiazepin-3-yl)ureido]benzoate

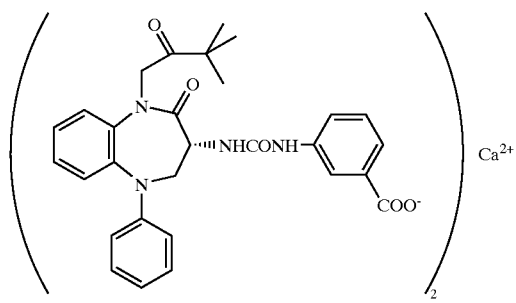

Step 1
Preparation of (R)-(–)-2-oxo-3-tert-butoxycarbonylamino-5-phenyl-1,3,4,5-tetrahydro-2H-1,5-benzodiazepine

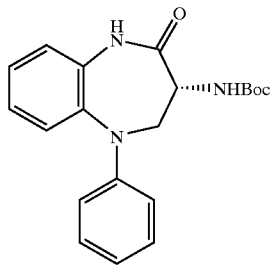

To a solution of 5 g of (R)-(+)-2-oxo-3-tert-butoxycarbonylamino-1,3,4,5-tetrahydro-2H-1,5-benzodiazepine in 25 ml of cyclohexanone were added 5.96 g of cyclooctene and 0.5 g of 10% palladium carbon. The mixture was stirred at the internal temperature of 145° C. for 2.5 hours. After the reaction mixture was cooled to room temperature, 20 ml of ethyl acetate was added. The mixture was filtered and the filtrate was concentrated under reduced pressure. The residue was crystallized by adding thereto diisopropyl ether and n-hexane and the resulting crystals were collected by filtration, whereby 3.2 g of the title compound was obtained.

Melting point: 160 to 165° C.

¹H-NMR (CDCl₃)δ: 1.43(9H,s), 3.67(1H,dd), 4.27(1H, dd), 4.57–4.65(1H,m), 5.60(1H,d), 6.69–6.90(3H,m), 7.09–7.25(6H,m), 7.60(1H,s)

[α]D²⁵: –233° (C=1.00, CHCl₃)

Step 2
Preparation of (R)-(–)-1-tert-butylcarbonylmethyl-2-oxo-3-amino-5-phenyl-1,3,4,5-tetrahydro-2H-1,5-benzodiazepine oxalate monohydrate

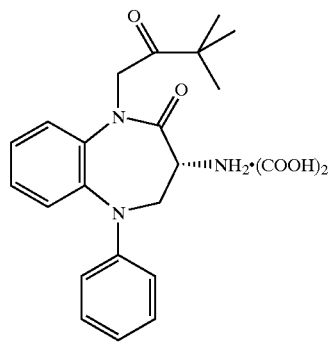

The title compound was obtained by a similar operation to Step 2 of Example 1 except for the use of (R)-(–)-2-oxo-3-tert-butoxycarbonylamino-5-phenyl-1,3,4,5-tetrahydro-2H-1,5-benzodiazepine instead of (R)-(–)-2-oxo-3-tert-butoxycarbonylamino-5-cyclohexyl-1,3,4,5-tetrahydro-2H-1,5-benzodiazepine, followed by a similar operation to Step 3 of Example 1.

Melting point: 130 to 135° C.

¹H-NMR (DMSO-d₆)δ: 1.17(9H,s), 3.90(1H,dd), 4.04–4.13(2H,m), 4.79(1H,d), 5.13(1H,d), 6.38(6H,br), 6.76 (2H,d), 6.88(1H,t), 7.12(1H,d), 7.21–7.34(5H,m).

[α]D²⁵: –56° (C=1.0, MeOH)

Elemental analysis: (C) 60.24, (H) 6.51, (N) 9.13 (C₂₁H₂₅N₃O₂·C₂H₂O₄·H₂O)

Step 3
Preparation of (R)-(−)-3-[3-(1-tert-butylcarbonylmethyl-2-oxo-5-phenyl-1,3,4,5-tetrahydro-2H-1,5-benzodiazepin-3-yl)ureido]benzoic acid

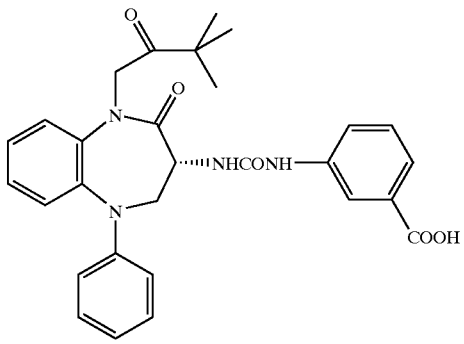

The title compound was obtained by carrying out an operation similar to the latter stage of Step 3 of Example 1 except for the use of (R)-(−)-1-tert-butylcarbonylmethyl-2-oxo-3-amino-5-phenyl-1,3,4,5-tetrahydro-2H-1,5-benzodiazepine oxalate monohydrate instead of (R)-1-tert-butylcarbonylmethyl-2-oxo-3-amino-5-cyclohexyl-1,3,4,5-tetrahydro-2H-1,5-benzodiazepine, followed by an operation similar to Step 5 of Example 1.

$^1$H-NMR (CDCl$_3$)δ: 1.29(9H,s), 3.72(1H,dd), 4.32(1H,d), 4.43(1H,dd), 4.81–4.90(1H,m), 5.23(1H,d), 7.13–8.41(13H, m), 7.50(1H,d), 8.29(1H,s), 10.71–10.77(1H,br).

[α]$D^{25}$: −134.8° (C=1.00, MeOH)

Step 4
Preparation of calcium (R)-(−)-3-[3-(1-tert-butylcarbonylmethyl-2-oxo-5-phenyl-1,3,4,5-tetrahydro-2H-1,5-benzodiazepin-3-yl)ureido]benzoate

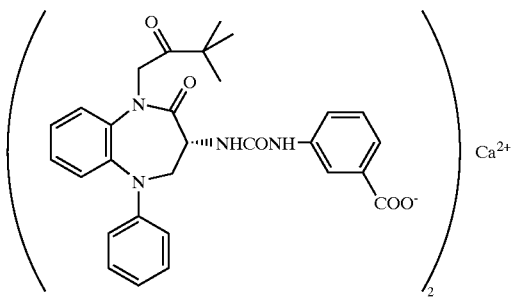

The title compound was obtained by carrying out an operation similar to Step 6 of Example 1 except for the use of (R)-(−)-3-[3-(1-tert-butylcarbonylmethyl-2-oxo-5-phenyl-1,3,4,5-tetrahydro-2H-1,5-benzodiazepin-3-yl)ureido]benzoic acid instead of (R)-(−)-3-[3-(1-tert-butylcarbonylmethyl-2-oxo-5-cyclohexyl-1,3,4,5-tetrahydro-2H-1,5-benzodiazepin-3-yl)ureido]benzoic acid.

$^1$H-NMR (DMSO-d$_6$)δ: 1.17(18H,s), 3.60(2H,dd), 4.00 (2H,dd), 4.55–4.65(2H,m), 4.75(2H,d), 5.11(2H,d), 6.77–6.93(8H,m), 7.12–7.35(14H,m), 7.50–7.57(4H,m), 7.88(2H,s), 9.20(2H,s).

MS(FAB)m/z: 1067 (MH$^+$), 553, 514

IR(KBr)cm$^{-1}$: 3368, 2969, 1664, 1552, 1500, 1397, 1296, 1240, 764

EXAMPLE 4
Preparation of calcium (R)-(−)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionate

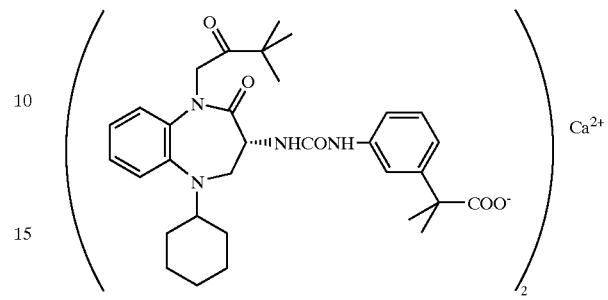

Step 1
Preparation of methyl 2-(4-chlorophenyl)-2-methylpropionate

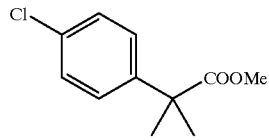

In 500 ml of N,N-dimethylformamide was suspended 38.7 g of 60% sodium hydride, followed by the dropwise addition of 50.0 g of 4-chlorophenylaceti c acid at room temperature in an argon gas atmosphere. The mixture was stirred at room temperature for 30 minutes. Under ice cooling, 167.3 g of methyl iodide was added dropwise and the resulting mixture was stirred at room temperature for 1 hour. The reaction mixture was poured into ice water, followed by extraction with ethyl acetate. The organic layer was washed successively with water and brine, dried over anhydrous magnesium sulfate and evaporated under reduced pressure, whereby 62.3 g of the title compound was obtained.

$^1$H-NMR (CDCl$_3$)δ: 1.56(6H,s), 3.66(3H,s), 7.24–7.31 (4H,m)

Step 2
Preparation of methyl 2-(4-chloro-3-nitrophenyl)-2-methylpropionate

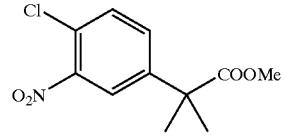

After dropwise addition of 40.0 g of concentrated nitric acid to 90.7 g of concentrated sulfuric acid under ice cooling, 62.3 g of methyl 2-(4-chlorophenyl)-2-methylpropionate was added dropwise. The resulting mixture was stirred at room temperature for 30 minutes. The reaction mixture was poured into ice water, followed by extraction with ethyl acetate. The organic layer was washed successively with water and brine, dried over anhydrous sodium sulfate and evaporated under reduced pressure, whereby 75.5 g of the title compound was obtained.

Melting point: 160 to 161° C.

$^1$H-NMR (DMSO-d$_6$)δ: 1.61(6H,s), 3.68(3H,s), 7.52(2H, s), 7.86(1H,s)

Step 3
Preparation of 2-(4-chloro-3-nitrophenyl)-2-methylpropionic acid

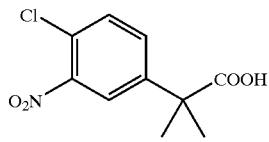

In 200 ml of methanol was dissolved 75.5 g of methyl 2-(4-chloro-3-nitrophenyl)-2-methylpropionate. Under ice cooling, 70 ml of an aqueous solution of 49.3 g of potassium hydroxide was added dropwise and the mixture was stirred at room temperature for 3 hours. The reaction mixture was concentrated under reduced pressure. To the residue were added water and n-hexane to separate the mixture into layers. Concentrated hydrochloric acid was added to the aqueous layer to adjust its pH to 2 or less, followed by extraction with ethyl acetate. The ethyl acetate layer was washed successively with water and brine, dried over anhydrous magnesium sulfate and evaporated under reduced pressure. The residue was recrystallized from ethyl acetate to obtain 53.1 g of the title compound.

$^1$H-NMR (CDCl$_3$)δ:1.64(6H,s), 7.50–7.58(2H,m), 7.91–7.92(1H,m)

Step 4
Preparation of 2-(3-aminophenyl)-2-methylpropionic acid hydrochloride

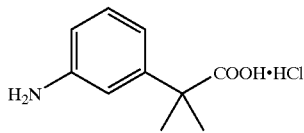

In 50 ml of methanol was dissolved 10.0 g of 2-(4-chloro-3-nitrophenyl)-2-methylpropionic acid. To the resulting mixture was added 1.0 g of 10% palladium carbon. In a hydrogen gas atmosphere, the mixture was stirred at room temperature for 3 hours. The reaction mixture was filtered and the filtrate was concentrated under reduced pressure to obtain 8.84 g of the title compound.

$^1$H-NMR (DMSO-d$_6$)δ:1.48(6H,s), 3.80(2H,brs), 7.22–7.26(1H,m), 7.35–7.48(3H,m), 10.20(2H,brs)

Step 5
Preparation of 2-methyl-2-(3-phenyloxycarbonylamino)phenylpropionic acid

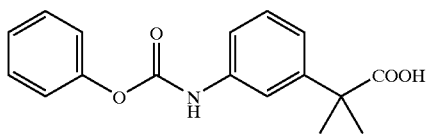

In a similar manner to Step 4 of Example 1 except for the use of 2-(3-aminophenyl)-2-methylpropionic acid hydrochloride instead of 3-aminobenzoic acid, the title compound was obtained.

$^1$H-NMR (CDCl$_3$)δ:1.59(6H,s), 6.79–6.94(1H,m), 7.04(1H,brs), 7.12–7.42(8H,m), 7.50(1H,brs)

Step 6
Preparation of (R)-(–)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionic acid

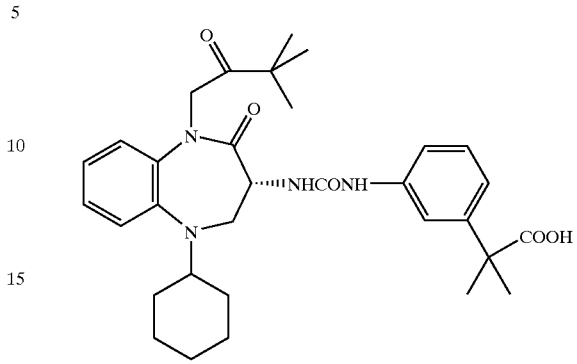

In a saturated aqueous solution of sodium bicarbonate was suspended 5.04 g of (R)-(–)-1-tert-butylcarbonylmethyl-2-oxo-3-amino-5-cyclohexyl-1,3,4,5-tetrahydro-2H-1,5-benzodiazepine oxalate to obtain the free base, followed by extraction with ethyl acetate. The organic layer was washed successively with a saturated aqueous solution of sodium bicarbonate and brine, dried over anhydrous sodium sulfate and evaporated under reduced pressure. The residue was dissolved in 12 ml of dimethylsulfoxide. To the resulting solution was added 3.0 g of 2-methyl-2-(3-phenyloxycarbonylamino)phenylpropionic acid, followed by stirring at 70° C. for 1 hour. After the reaction mixture was cooled to room temperature, 100 ml of ethyl acetate was added. The resulting mixture was then washed successively with a 1N aqueous solution of sodium hydroxide, 1N hydrochloric acid and brine, dried over anhydrous sodium sulfate and evaporated under reduced pressure. A 1:1 mixed solvent of toluene and heptane was added to the residue for crystallization. Crystals so precipitated were collected by filtration and dried, whereby 3.99 g of the title compound was obtained.

Melting point: 139 to 144° C.
$^1$H-NMR (CDCl$_3$) δ:1.13–2.04(25H,m), 3.15–3.35(2H,m), 3.64–3.70(1H,m), 4.20(1H,d), 4.64–4.73(1H,m), 5.06(1H,d), 6.74(1H,d), 6.96–7.22(7H,m), 7.50–7.53(1H,m), 7.58(1H,s)
[α]D$^{23}$: –111° (C=1.03, CHCl$_3$)

Step 7
Preparation of calcium (R)-(–)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionate

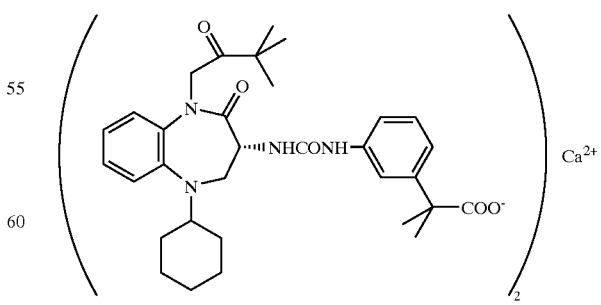

The title compound was obtained in a similar manner to Step 6 of Example 1 except for the use of (R)-(–)-2-[3-[3-(1-tert-butylcarbonylmethyl-2-oxo-5-cyclohexyl-1,3,4,5- tetrahydro-2H-1,5-benzodiazepin-3-yl)ureido]phenyl]-2-methylpropionic acid instead of (R)-(-)-3-[3-(1-tert-butylcarbonylmethyl-2-oxo-5-cyclohexyl-1,3,4,5-tetrahydro-2H-1,5-benzodiazepin-3-yl)ureido]benzoic acid.

$^1$H-NMR (DMSO-d$_6$)δ:1.17(18H,s), 1.34(12H,s), 1.08–1.82(18H,m), 1.92–2.05(2H,m), 3.13–3.45(6H,m), 4.31–4.43(4H,m), 5.11(2H,d), 6.64(2H,d), 6.90–7.35(16H,m), 8.95(2H,s).

MS(FAB)m/z: 1163(MH$^+$)

IR(KBr)cm$^{-1}$: 3300, 2932, 2857, 1727, 1665, 1497, 1406, 1366, 1215, 756, 702

$[\alpha]D^{26}$: −66.1 (C=1, MeOH)

Elemental analysis: (C) 63.95, (H) 7.50, (N) 9.21, (Ca) 3.24 ($C_{64}H_{82}N_8O_{10}Ca$)

Test 1

Test on Inhibition of Pentagastrin-stimulated Gastric Acid Secretion

Male Sprague-Dawley (SD)-strain rats were used. Under anesthesia with ether, each rat was subjected to the operation for pylorus ligation and placement of a duodenal catheter and gastric fistula. After completion of the operation, each rat was held in a Bollman-type cage and constantly infused with 15 μg/kg/hr of pentagastrin through the tail vein. Test compounds were suspended in a 0.5% sodium carboxymethylcellulose solution (which will hereinafter be called "vehicle"). Administration of the vehicle or test compound was carried out through the intraduodenal catheter 1 hour after the beginning of pentagastrin infusion. Acidity of the collected gastric juice was measured by an automatic titrator. Acid output was determined by multiplying the volume of gastric juice by its acidity. Inhibition of acid output for 3 hours from 1 to 4 hours after administration of the test compound was calculated by the following equation.

Inhibition (%)=(mean acid output of vehicle administered group−mean acid output of compound group)/mean acid output of vehicle administered group×100

Results are shown in Table 1 and 2.

TABLE 1

| Test compound | Dose (mg/kg) | Inhibition of acid output (%) |
|---|---|---|
| Compound of Example 1 (Ca salt) | 0.03 | 42.3 |
| Compound of Example 1 in the free form (*1) | 0.03 | 4.8 |

(*1): Compound of Example 143 in WO98/25911

TABLE 2

| Test compound | Dose (mg/kg) | Inhibition of acid output (%) |
|---|---|---|
| Compound of Example 4 (Ca salt) | 0.03 | 46.1 |
| Compound of Example 4 in the free form (*2) | 0.03 | 13.7 |

*1: Compound of Example 2 in WO99/64403

Test 2

Binding Test to CCK-B Receptor

The cerebral cortex excised from a Hartley-strain male guinea pig was homogenized in 50 times the amount of a 50 mM Tris-HCl buffer (pH 7.4), followed by centrifugal separation at 50000×g for 10 minutes. Addition of the same amount of the same buffer to the precipitate thus obtained and centrifugation were repeated 2 times. The final precipitate was homogenized in a 10 mM HEPES buffer (pH 6.5) containing 5 mM magnesium chloride, 1 mM EGTA, 0.25 mg/ml bacitracin and 130 mM sodium chloride, and used as the receptor preparation.

Binding assay was conducted by adding, to 50 μl of a test compound solution, 50 μl of a [$^3$H]CCK-8 solution having the final concentration of 1.0 nM and 900 μl of the receptor preparation (protein content: 800 μg/tube) and reacting them at 25° C. for 2 hours. After completion of the reaction, the mixture was suction filtrated through a Whatman GF/B filter treated in advance with 0.1% BSA. Rightly after filtration, the filter was washed four times, each with 3 ml of ice-cold 50 mM Tris-HCl buffer (pH 7.4). After a scintillator was added to the filter and the resulting filter was then allowed to stand for a day, radioactivity on the filter was measured by a liquid scintillation counter. The binding of [$^3$H]CCK-8 in the presence of 1 μM CCK-8 when the test compound was not added was defined as non-specific binding. The difference between the total binding (in the absence of CCK-8) and non-specific binding was defined as specific binding. The concentration (IC$_{50}$) of the test compound inhibiting 50% of the specific binding of [$^3$H]CCK-8 was calculated.

Results are shown in Tables 3.

TABLE 3

| Test compound | IC$_{50}$ (nM) |
|---|---|
| Compound of Example 1 (Ca salt) | 1.68 |
| Compound of Example 1 in the free form (*1) | 1.45 |

(*1) Compound of Example 143 in WO98/25911

Test 3 (Test on Hygroscopicity under High Humidity Conditions)

(1) A saturated aqueous solution of potassium sulfate was charged in a desiccator and was allowed to stand for at least one day in a temperature controlled room set at 25° C. The sample (0.5 g) was stored and weighed. Hygroscopicity was measured by its weight change. The relative humidity at that time was 97.3% RH.

As a result, Compound of Example 1 (Ca salt) exhibited lower hygroscopicity than the Na salt corresponding thereto (Na salt of Compound of Example 143 in WO98/25911).

TABLE 4

| | Weight change (%) when stored at 25° C. and 97.3% RH | | | | | | |
|---|---|---|---|---|---|---|---|
| | Storage time (day) | | | | | | |
| Sample | 0 | 1 | 2 | 3 | 4 | 10 | 14 |
| Compound of Example 1 (Ca salt) | 0 | 4.61 | 5.00 | 4.94 | 4.97 | 5.43 | 5.41 |
| Na salt corresponding thereto (*3) | 0 | 19.51 | 24.90 | 28.70 | 31.09 | 42.84 | 45.55 |

(*3): Na salt of Compound of Example 143 in WO98/25911

(2) A saturated aqueous solution of potassium sulfate was charged in a desiccator and was allowed to stand for at least one day in a temperature controlled room set at 25° C. The sample (0.1 g) was stored and weighed. Hygroscopicity was measured by its weight change. The relative humidity at that time was 97.3% RH.

As a result, Compound of Example 4 (Ca salt) exhibited lower hygroscopicity than the Na salt corresponding thereto (Compound of Example 5 in WO99/64403).

TABLE 5

Weight change (%) when stored at 25° C. and 97.3% RH

| Sample | Storage days | | | | | | | |
|---|---|---|---|---|---|---|---|---|
| | 0 | 2 | 4 | 7 | 9 | 11 | 18 | 30 |
| Compound of Example 4 (Ca salt) | 0 | 8.15 | 7.87 | 8.38 | 9.07 | 8.14 | 8.51 | 8.23 |
| Na salt corresponding thereto (*4) | 0 | 21.23 | 23.85 | 23.04 | 24.36 | 24.31 | 26.06 | 25.23 |

(*4): Compound of Example 5 in WO99/64403

Toxicity Test

SD male 5.5-week-old rats were used and one group consisted of 3 rats. After suspending the compound of each Example in 0.5% methyl cellulose, 1000 mg/kg of the resulting suspension was orally administered. Observation was conducted for one week, but no death was observed in each administered group.

Preparation Example 1

| Compound of Example 3 | 20 g |
|---|---|
| Lactose | 315 g |
| Corn starch | 125 g |
| Crystalline cellulose | 25 g |

The above-described ingredients were mixed uniformly. To the resulting mixture was added 200 ml of a 7.5% aqueous solution of hydroxypropyl cellulose. By an extruding granulator equipped with a screen of 0.5 mm in diameter, the mixture was granulated and rightly after that, the granulated mixture was rounded by a Marumerizer and dried, whereby granules were obtained.

Preparation Example 2

| Compound of Example 1 | 20 g |
|---|---|
| Lactose | 100 g |
| Corn starch | 36 g |
| Crystalline cellulose | 30 g |
| Carboxymethylcellulose calcium | 10 g |
| Magnesium stearate | 4 g |

The above-described ingredients were mixed uniformly, followed by tableting by a single-punch tableting machine having a punch of 7.5 mm in diameter into tablets, each 200 mg in weight.

Preparation Example 3

| Compound of Example 4 | 100 mg |
|---|---|
| Sodium acetate | 2 mg |
| Acetic acid (for adjusting pH to 5.8) | q.s. |
| Distilled water | q.s. |
| | total 10 ml/vial |

According to the above-described formulation, an injection was prepared.

Industrial Applicability

The invention compounds have potent gastric acid secretion inhibitory action and strong gastrin and/or CCK-B receptor antagonism, and are favorable as a pharmaceutical from the viewpoint of quality maintenance because of low hygroscopicity and easy purification. They can therefore be used for treatment, amelioration, prevention of diseases related to the above-described actions such as gastric ulcer, duodenal ulcer, gastritis, reflux esophagitis, pancreatitis, Zollinger-Ellison syndrome, antral G-cell hyperplasia, basal-mucous-membrane hyperplasia, cholecystitis, attack of biliary colic, gastrointestinal dysmotility, irritable bowel syndrome, certain types of tumors, eating disorders, anxiety, panic disorder, depression, schizophrenia, Parkinson's disease, tardive dyskinesia, Gilles de la Tourette syndrome, drug dependence, and drug-withdrawal symptoms; and induction of pain relief or facilitation of induction of pain relief by use of an opioid drug.

What is claimed is:

1. A calcium salt of a 1,5-benzodiazepine compound represented by the following formula (I):

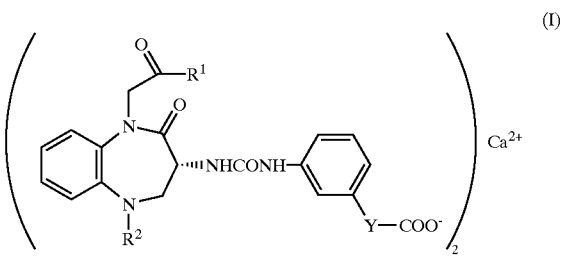

wherein, $R^1$ represents a lower alkyl group, $R^2$ represents a phenyl or cyclohexyl group, and Y represents a single bond or a lower alkylene group.

2. The calcium salt of claim 1, wherein $R^1$ represents a t-butyl group, $R^2$ represents a cyclohexyl group and Y represents a single bond or a dimethylmethylene group.

3. The calcium salt of claim 1, which is calcium (R)-(−)-3-[3-(1-tert-butylcarbonylmethyl-2-oxo-5-cyclohexyl-1,3,4,5-tetrahydro-2H-1,5-benzodiazepin-3-yl)ureido]benzoate.

4. A pharmaceutical composition, which comprises the calcium salt as claimed in claim 1 and at least one pharmaceutically acceptable carrier.

5. A method for treating a digestive tract disease resulting from the excessive secretion of gastric acid, which comprises administering an effective amount of the calcium salt as claimed in claim 1 to a mammal in need thereof.

6. A process for preparing a calcium salt of a 1,5-benzodiazepine compound represented by the following formula (I):

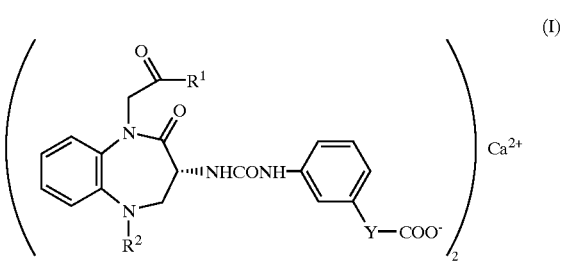

wherein, $R^1$ represents a lower alkyl group, $R^2$ represents a phenyl or cyclohexyl group and Y represents a single bond or a lower alkylene group, which comprises adding aqueous ammonia to a 1,5-benzodiazepine compound represented by the following formula (II):

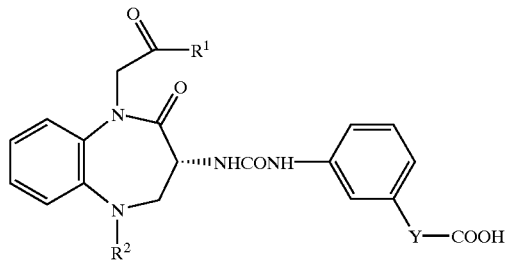

(II)

wherein, $R^1$, $R^2$ and Y have the same meanings as defined above, and then treating the resulting mixture by the addition of calcium chloride.

7. A process for preparing a 1,5-benzodiazepine compound represented by the following formula (II):

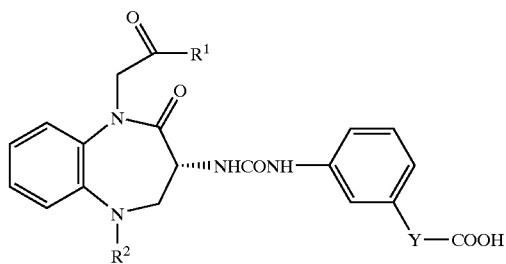

(II)

wherein, $R^1$ represents a lower alkyl group,
$R^2$ represents a phenyl or cyclohexyl group and
Y represents a single bond or a lower alkylene group, which comprises
reacting an oxalate of a 3-amino-1,5-benzodiazepine compound represented by the following formula (III):

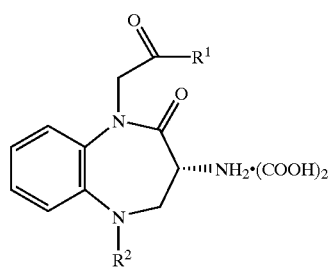

(III)

wherein, $R^1$ and $R^2$ have the same meanings as defined above,
with a compound represented by the following formula (IV):

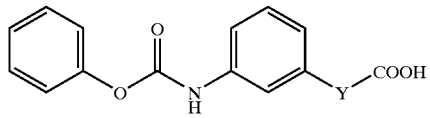

(IV)

wherein, Y has the same meaning as defined above.

8. A process for preparing a calcium salt of a 1,5-benzodiazepine compound represented by the following formula (I):

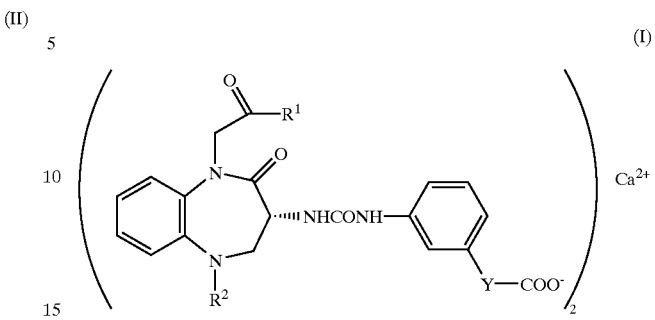

(I)

wherein, $R^1$ represents a lower alkyl group,
$R^2$ represents a phenyl or cyclohexyl group and
Y represents a single bond or a lower alkylene group, which comprises
reacting an oxalate of a 3-amino-1,5-benzodiazepine compound represented by the following formula (III):

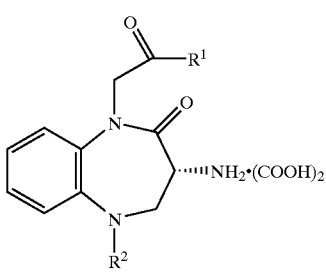

(III)

wherein, $R^1$ and $R^2$ have the same meanings as defined above,
with a compound represented by the following formula (IV):

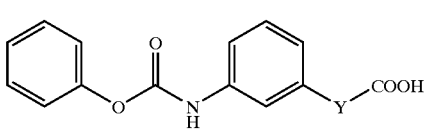

(IV)

wherein, Y has the same meaning as defined above,
adding aqueous ammonia to the resulting 1,5-benzodiazepine compound represented by the following formula (II)

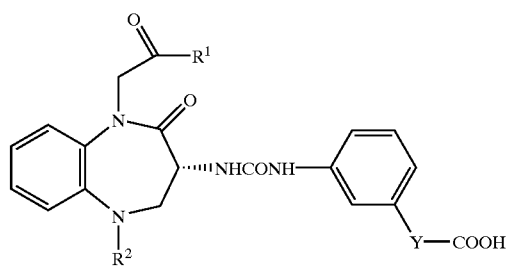

(II)

wherein, $R^1$, $R^2$ and Y have the same meanings as defined above and then treating the resulting derivative by the addition of calcium chloride.

9. A process for preparing a 1,5-benzodiazepine compound represented by the following formula (II):

(II)

wherein, $R^1$ represents a lower alkyl group, $R^2$ represents a phenyl or cyclohexyl group and Y represents a single bond or a lower alkylene group, which comprises reacting an oxalate of a 3-amino-1,5-benzodiazepine compound represented by the following formula (III):

(III)

wherein, $R^1$ and $R^2$ have the same meanings as defined above with a compound represented by the following formula (IX):

(IX)

wherein, X represents a halogen atom and then reacting the resulting 3-phenoxycarbonylamino compound represented by the following formula (X):

(X)

wherein, $R^1$ and $R^2$ have the same meanings as defined above, with a 3-substituted aniline compound represented by the following formula (XI):

(XI)

wherein, $R^3$ represents a hydrogen atom or a metal atom and

Y has the same meaning as defined above.

10. A process for preparing a calcium salt of a 1,5-benzodiazepine compound represented by the following formula (I):

(I)

wherein, $R^1$ represents a lower alkyl group, $R^2$ represents a phenyl or cyclohexyl group, and Y represents a single bond or a lower alkylene group, which comprises reacting an oxalate of a 3-amino-1,5-benzodiazepine compound represented by the following formula (III):

(III)

wherein, $R^1$ and $R^2$ have the same meanings as defined above, with a 3-substituted aniline compound represented by the following formula (XI):

(IX)

wherein, X represents a halogen atom;

reacting the resulting 3-phenoxycarbonylamino compound represented by the following formula (X):

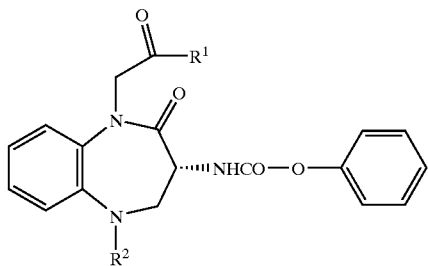

(X)

wherein, $R^1$ and $R^2$ have the same meanings as defined above, with a 3-substituted aniline compound represented by the following formula (XI):

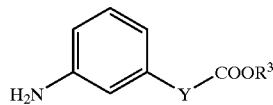

(XI)

wherein, $R^3$ represents a hydrogen atom or a metal atom and Y has the same meaning as defined above;

adding aqueous ammonia to the resulting 1,5-benzodiazepine compound represented by the following formula (II):

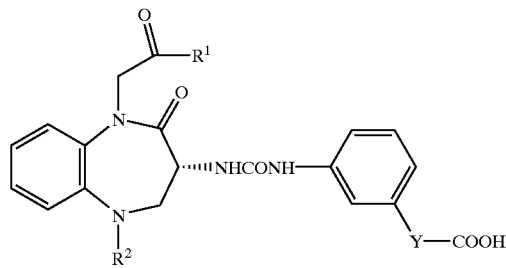

(II)

wherein, $R^1$, $R^2$ and Y have the same meanings as defined above, and then treating the resulting mixture by adding thereto calcium chloride.

11. The calcium salt of claim 1, which is calcium (R)-(−)-2-[3-[3-(1-tert-butylcarbonylmethyl-2-oxo-5-cyclohexyl-1,3,4,5-tetrahydro-2H-1,5-benzodiazepin-3-yl)ureido]phenyl]-2-methylpropionate.

12. A pharmaceutical composition which comprises the calcium salt as claimed in claim 2 and at least one pharmaceutically acceptable carrier or diluent.

13. A pharmaceutical composition which comprises the calcium salt as claimed in claim 3 and at least one pharmaceutically acceptable carrier or diluent.

14. A pharmaceutical composition which comprises the calcium salt as claimed in claim 3 and at least one pharmaceutically acceptable carrier or diluent.

15. The method as claimed in claim 5 wherein the digestive track disease is at least one selected from the group consisting of gastric ulcer, duodenal ulcer, gastritis, reflux esophagitis and Zollinger-Ellison syndrome.

16. The method as claimed in claim 5, wherein the calcium salt is administered orally.

17. The method as claimed in claim 5, wherein the calcium salt is administered parenterally.

18. The method as claimed in claim 16, wherein the calcium salt is administered in an amount of from 1 to 1000 mg per day.

19. The method as claimed in claim 16, wherein the calcium salt is administered in from 1 to 3 portions a day.

20. The method as claimed in claim 17, wherein the calcium salt is administered in combination with at least one selected from the group consisting of water, ethanol, glycerin and a surfactant.

21. The method as claimed in claim 5, wherein the calcium salt is administered in an amount effective for inhibitory action against secretion of gastric acid.

22. The method as claimed in claim 5, wherein the calcium salt is administered in an amount effective for inhibiting gastric acid output by an amount of from 42.3 to 46.1% from 1 to 4 hours after administering the calcium salt.

23. The method as claimed in claim 5, wherein $R^1$ represents a t-butyl group, $R^2$ represents a cyclohexyl group, and Y represents a single bond or a dimethylmethylene group.

24. The method as claimed in claim 5, wherein the calcium salt is calcium (R)-(−)-1-3-[3-(1-tert-butylcarbonylmethyl-2-oxo-5-cyclohexyl-1,3,4,5-tetrahydro-2H-1,5-benzodiazepin-3-yl)ureido]benzoate.

25. The method as claimed in claim 5, wherein the calcium salt is calcium (R)-(−)-2-[3-[3-(1-tert-butylcarbonylmethyl-2-oxo-5-cyclohexyl-1,3,4,5-tetrahydro-2H-1,5-benzodiazepin-3yl)ureido]phenyl]-2-methylpropionate.

* * * * *